(12) United States Patent
Wright

(10) Patent No.: US 11,944,394 B1
(45) Date of Patent: Apr. 2, 2024

(54) SYSTEMS, DEVICES, AND METHODS FOR PERFORMING GUIDED COMPUTERIZED TOMOGRAPHY (CT) ANESTHETIC TREATMENT OF A NASAL CAVITY PRIOR TO PERFORMING A SINUPLASTY BALLOON SURGERY

(71) Applicant: James T. Wright, McAllen, TX (US)

(72) Inventor: James T. Wright, McAllen, TX (US)

(73) Assignee: James T. Wright, McAllen, TX (US)

( * ) Notice: Subject to any disclaimer, the term of this patent is extended or adjusted under 35 U.S.C. 154(b) by 0 days.

(21) Appl. No.: 18/210,613

(22) Filed: Jun. 15, 2023

(51) Int. Cl.
| | |
|---|---|
| *A61B 5/05* | (2021.01) |
| *A61B 6/03* | (2006.01) |
| *A61B 34/20* | (2016.01) |
| *A61M 19/00* | (2006.01) |
| *A61B 90/00* | (2016.01) |
| *A61M 25/01* | (2006.01) |

(52) U.S. Cl.
CPC .............. *A61B 34/20* (2016.02); *A61B 6/032* (2013.01); *A61M 19/00* (2013.01); *A61B 2034/2051* (2016.02); *A61B 2090/3762* (2016.02); *A61M 25/0108* (2013.01); *A61M 2025/0166* (2013.01); *A61M 2210/0618* (2013.01)

(58) Field of Classification Search
CPC ........... A61B 34/20; A61B 2034/2051; A61M 25/0108; A61M 2025/0166; A61M 2210/0618
See application file for complete search history.

(56) References Cited

U.S. PATENT DOCUMENTS

| | | | |
|---|---|---|---|
| 2006/0210605 A1 * | 9/2006 | Chang ................ | A61B 17/1688 604/510 |
| 2018/0153373 A1 * | 6/2018 | Friedlander ............ | A61B 1/233 |
| 2019/0167351 A1 * | 6/2019 | Salazar .................. | A61B 5/062 |

* cited by examiner

*Primary Examiner* — Joel F Brutus
(74) *Attorney, Agent, or Firm* — Foley & Lardner LLP

(57) ABSTRACT

A method of applying a topical numbing agent to a nasal cavity without sedating a patient may include inserting a catheter into a nostril of the patient, the catheter having a first bend that forms a first angle such that at least a portion of the catheter is non-linear. The method may also include guiding a distal end of the catheter into the nasal cavity using a computerized tomography (CT) system by aligning a distal end of the catheter with a first cavity portion of the nasal cavity using a projection of the catheter within the nasal cavity on a CT scan of the patient, and moving the catheter within the nasal cavity while dynamically displaying the projection of the catheter by the CT system relative to the nasal cavity. The method may further include dispensing the topical numbing agent through the catheter into the first cavity portion.

13 Claims, 6 Drawing Sheets

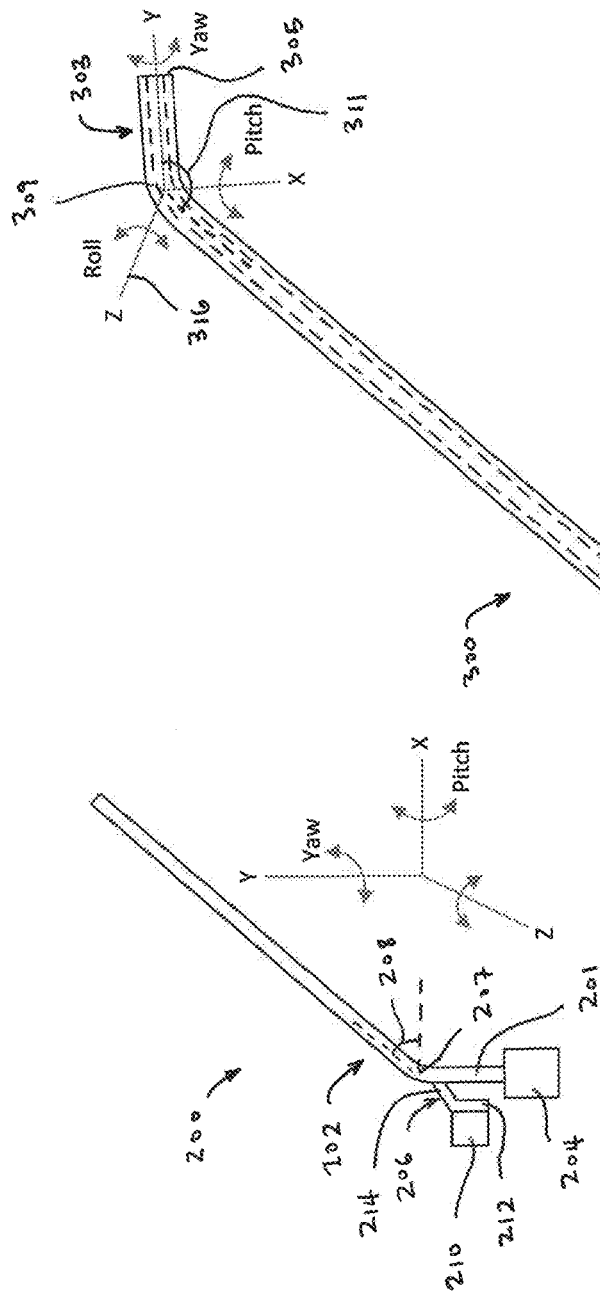
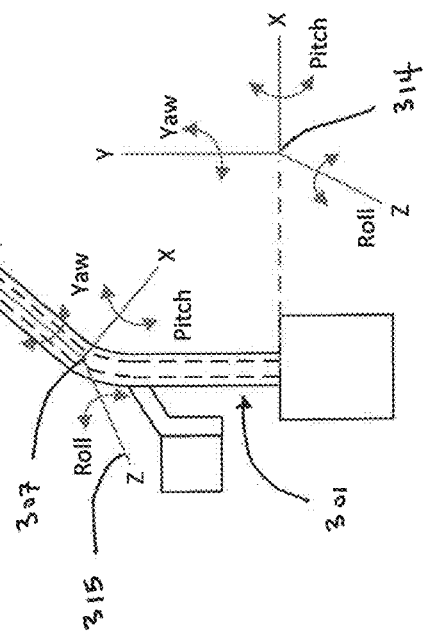
FIG. 2
FIG. 3

SYSTEMS, DEVICES, AND METHODS FOR PERFORMING GUIDED COMPUTERIZED TOMOGRAPHY (CT) ANESTHETIC TREATMENT OF A NASAL CAVITY PRIOR TO PERFORMING A SINUPLASTY BALLOON SURGERY

BACKGROUND

Nasal/sinus treatments, including nasal sinuplasty balloon surgeries, cryoablation therapy, and other procedures exist for treatment of various sinus issues, including acute sinusitis, allergic/non-allergic rhinitis, and other diseases and conditions of the nose and the paranasal sinuses. Such treatments are becoming more common for the treatment of sinus conditions and are typically performed on an outpatient basis. For skilled ear, nose, and throat practitioners, the procedure after anesthetic is applied generally takes just minutes to perform.

When performing sinuplasty balloon surgeries, the patient has to be prepared with an anesthetic, either a mild general anesthetic or a local anesthetic. As understood, a mild general anesthetic, which is currently used by about 50% of physicians who perform sinuplasty balloon surgeries, can be dangerous due to possible undesirable reactions by some patients. Local anesthetics can be painful for the patient due to typically applying the local anesthetic using a syringe within the nasal cavity. While it is possible to topically apply a local anesthetic, such application is often difficult and typically results in discomfort to the patient due to challenges faced by the surgeon as the doctor has to apply the topical anesthetic "blindly" due to not being able to easily see within the nasal cavities. As such, there is a need to improve how physicians administer anesthetics to patients prior to performing sinuplasty balloon surgeries.

SUMMARY

To provide for improved patient care in anesthetizing a patient prior to sinuplasty balloon surgery, the principles provided herein provide for the use of a guided computerized tomography (CT) device using a catheter through which local anesthetic or numbing agent may be applied. The guided catheter may be bent so as to conform to the nasal passageways and a CT scanner may be configured to account for the bent guided catheter so that the surgeon is more able (i) to determine where to apply the local anesthetic and (ii) to more accurately apply the local anesthetic in the region desired by the surgeon. By using such a guided catheter technique, the risk associated with general anesthesia is avoided and the patient pain when applying anesthetic using a syringe is also avoided. To accommodate for one or more bend(s) along the catheter, the CT scanner may be configured with the geometry of the catheter so as to graphically represent a projection along a longitudinal axis of a tip of the catheter from which local anesthetic is released.

One embodiment of the present disclosure relates to a CT guided device that includes a catheter and a position sensor. The catheter has a proximal end, a distal end, and a shaft extending between the proximal end and the distal end. The shaft may include a bend that forms a first angle such that at least a portion of the catheter is non-linear. The position sensor may be coupled to the catheter at the proximal end and be configured (i) to sense a position and/or orientation of the catheter, and (ii) to generate position data representative of the position and/or orientation.

Another embodiment of the present disclosure relates to a method of applying a topical numbing agent to a nasal cavity without sedating a patient. The method includes inserting a catheter into a nostril of the patient, the catheter having a first bend that forms a first angle such that at least a portion of the catheter is non-linear. The method also includes guiding a distal end of the catheter into the nasal cavity using a CT system by (i) aligning a distal end of the catheter with a first cavity portion of the nasal cavity using a projection of the catheter within the nasal cavity on a CT scan of the patient, and (ii) moving the catheter within the nasal cavity while dynamically displaying the projection of the catheter by the CT system relative to the nasal cavity. The method further includes dispensing the topical numbing agent through the catheter into the first cavity portion.

Yet another embodiment of the present disclosure relates to a CT system that includes a guided catheter, a position sensor, and a controller. The guided catheter includes at last one bend positioned between a base portion of the guided catheter and a tip of the guided catheter. The position sensor may be coupled to the guided catheter and be configured to sense a position and/or orientation of the guided catheter and to generate position signals representative of the position and/or orientation of the guided catheter. The controller may be in communication with the position sensor to receive the position signals and be configured to (i) generate a CT scan of an anatomical region of a patient, (ii) display an image of the anatomical region of the patient on an electronic display, (iii) dynamically display a graphical representation of the position of the guided catheter with the at least one bend on the CT scan relative to the image of the anatomical region on the electronic display, and (iv) display a graphical projection indicator from the tip of the guided catheter on the CT scan.

Yet another embodiment of the present disclosure relates to a method for operating a CT system. The method may include setting, by a controller of the CT system, a physical configuration of a guided catheter having a bend such that the guided catheter forms an angle. The method also includes displaying an image of an anatomical region of a patient on an electronic display of the CT scanner, and receiving position signals from a position sensor connected to the guided catheter. The method may additionally include displaying a graphical representation of the guided catheter relative to the image of the anatomical region of the patient being displayed in real-time. The method further includes generating a graphical projection indicator from a tip (e.g., extending along a longitudinal axis of the tip) of the guided catheter as a function of the physical configuration of the guided catheter, where the graphical projection indicator is angularly oriented from an axial axis of a base portion prior to the bend of the guided catheter, and displaying the graphical projection indicator from a graphical representation of a tip of the guided catheter being displayed on the electronic display.

BRIEF DESCRIPTION OF THE FIGURES

A more complete understanding of the method and apparatus of the present invention may be obtained by reference to the following Detailed Description when taken in conjunction with the accompanying figures wherein:

FIG. 2 is a side view of an illustrative guided catheter with a single bend;

FIG. 3 is a side view of another illustrative guided catheter with two bends;

DETAILED DESCRIPTION

Before turning to the figures, which illustrate certain illustrative embodiments in detail, it should be understood that the present disclosure is not limited to the details or methodology set forth in the description or illustrated in the figures. It should also be understood that the terminology used herein is for the purpose of description only and should not be regarded as limiting.

Figure 1:
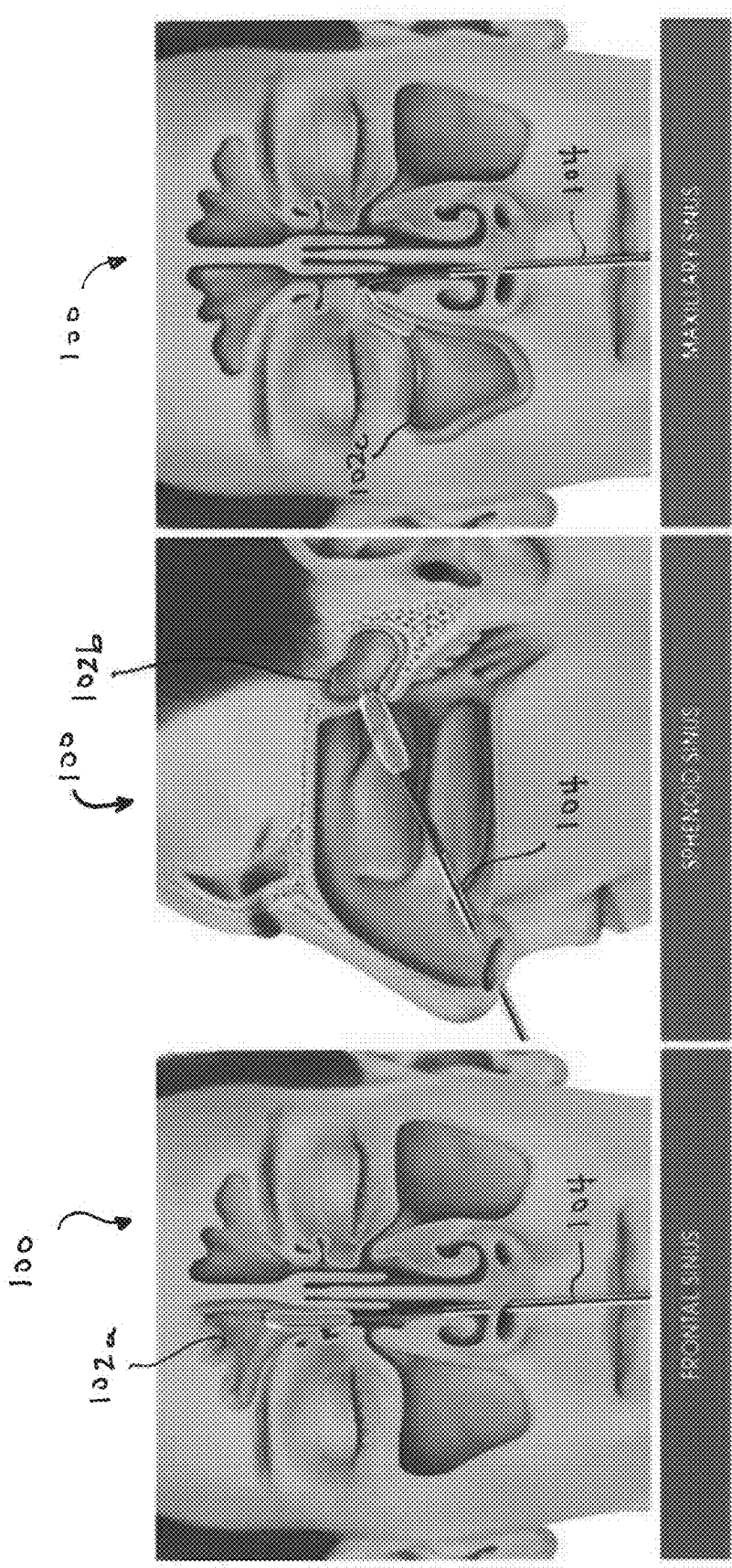
FIG. 1A is a front partial view of a frontal sinus cavity of a patient during a nasal treatment operation.
FIG. 1B is a side partial view of a sphenoid sinus cavity of a patient during a nasal treatment operation.
FIG. 1C is a front partial view of a maxillary sinus cavity of a patient during a nasal treatment operation.

Surgical intervention for nasal/sinus treatments generally involve the use of a small device, probe, or catheter into the nasal cavity to provide localized treatment to clogged or blocked nasal passages. For example, FIG. 1A shows a treatment of a patient 100 with a blocked nasal passage in a frontal sinus 102a via balloon sinuplasty in which a small, catheter-guided balloon 104 is inserted into the passage and inflated to expand the passage to the frontal sinus 102a and open up the nasal cavity. FIG. 1B and FIG. 1C show similar treatments being applied to expand nasal passages in the sphenoid sinus 102b (FIG. 1B) and the maxillary sinus 102c (FIG. 1C) regions of the patient 100. Other minimally invasive sinus treatments include cryoablation for treatment of chronic rhinitis and other sinus conditions that involve application of a cryoprobe at low temperature to freeze nerves or other tissue.

Referring to the figures generally, a method of treating nasal/sinus conditions using CT guidance is provided. The method includes using a CT system and CT guided device that is specifically tailored for use in performing nasal/sinus treatments. The CT guided device may be a guided catheter that can be used, according to the methods described herein, to apply a topical anesthetic (e.g., Tetracaine, etc.) into a nasal/sinus cavity of a patient. The guided catheter can facilitate delivery of the topical anesthetic to different areas of the sinuses more efficiently (e.g., using less anesthetic), more accurately (i.e., placed in locations as desired by the surgeon), and without sedating the patient or injecting the patient with anesthetics near or at the treatment area. The CT guided device can also be used to facilitate other nasal/sinus treatments, for example, to guide application of a cryoprobe or other instruments for use in nasal cryotherapy, or in balloon sinuplasty to guide positioning of a balloon into a clogged or contracted nasal passage. The CT guided device provides for more accurate placement of the topical anesthetic by a physician (e.g., a surgeon).

Referring to FIG. 2, a CT guided device 200 is shown that is configured for treatment of various nasal/sinus conditions. The CT guided device 200 may include a catheter or another form of delivery device for insertion into canals, vessels, passageways, or body cavities so as to permit dispensing or injection of fluids. For example, the CT guided device may be configured to dispense a topical numbing agent to a tissue surface within a nasal cavity. The catheter may also be configured to facilitate insertion of a balloon or cryoprobe into a passage for application of different treatments. Although the principles described herein are primarily focused on nasal cavities, it should be understood that the principles may be extended to treating other anatomical regions of patients.

As shown in FIG. 2, the CT guided device 200 includes a catheter 202, a connecting element 204, and a sensor mount 206. The catheter 202 is configured to deliver fluids from a fluid transfer device that is coupled to the CT guided device 200 (e.g., a syringe, etc.). The catheter 202 is sized for insertion into a nasal cavity/passage and includes a proximal end (e.g., a first end, inner end, base end, etc.), a distal end (e.g., a second end, outer end, treatment end, etc.), and a shaft extending therebetween. The shaft may form a hollow tube that is configured to fluid transfer fluids to and/or from a treatment area, such as a nasal cavity and/or passage (see also FIG. 3).

As shown in FIG. 2, the proximal end of the shaft and/or catheter 202 may define a base portion 201 or base of the shaft that is coupled to the connecting element 204, and extends axially away from the connecting element 204 along a Y-axis direction (e.g., vertically upward from the connecting element 204 as shown in FIG. 2). The distal end defines a tip of the shaft at an outer end surface of the shaft and an opening (e.g., an outlet, etc.) through which fluids may be delivered to the nasal cavity and/or passage.

The shaft includes at least one bend, shown as first bend 207 disposed between the proximal end and the distal end. The first bend 207 may form a first angle 208 such that at least a portion of the shaft is non-linear (e.g., non-perpendicular to the X-axis as shown in FIG. 2). In some embodiments, the shaft is a curvilinear shaft that is characterized by curved lines between the proximal end and the distal end. The first bend 207 with the first angle 208 may be configured (e.g., angle set to a particular number of degrees and having a certain curvature) to facilitate entry into one or more nasal cavities and/or passages. For example, the first angle 208 may be configured (e.g., starting at a certain distance from the connecting element 204) based on an average distance between an entry to a patient's nose and a frontal sinus passage, or another cavity and/or passage within the patient's nose. The first angle 208 may be within a range between approximately 15 degrees and approximately 30 degrees, approximately 30 degrees and approximately 45 degrees, approximately 45 degrees and approximately 75 degrees, inclusive, or another angle between and including the foregoing ranges (e.g., between approximately 55 degrees and approximately 65 degrees, approximately 60 degrees, etc.). The shaft may include additional bends in other embodiments to facilitate treatment of other areas within a patient's nose or in another anatomical region.

The connecting element 204 may be configured to fluidly couple the shaft (e.g., the base portion 201 of the shaft at a proximal end of the shaft, etc.) with a fluid transfer device. The fluid transfer device may be a syringe (see FIG. 4) configured to transfer fluid into the shaft and/or to draw fluids out from the nasal cavity and/or passage. In other embodiments, the fluid transfer device may be a fluid conduit, such as flexible tubing. The connecting element 204 may include a tube fitting, such as a barb connector, a push-to-connect pneumatic fitting, a compression tube fitting, a threaded fitting, such as a national pipe thread (NPT) fitting or another suitable connector. The connecting element 204 may be welded to the shaft, integrally formed with the shaft from a single piece of material, or otherwise coupled to the shaft.

The sensor mount 206 is configured to couple a position sensor 210 to the shaft and/or catheter 202. The sensor mount 206 may include a pedestal 212 and a support member 214 extending between the pedestal 212 and the base portion 201 of the shaft. The support member 214 may be coupled to the base portion 201 adjacent to the proximal end of the shaft and may extend away from the shaft at an angle. The pedestal 212 may be coupled to the support member 214 and may be spaced apart from the shaft by the support member 214. It should be appreciated that the location and/or orientation of the sensor mount 206 may be different in other embodiments. For example, the sensor mount 206 may be coupled to the connecting element 204 or may extend away from the connecting element 204 and/or the shaft in a perpendicular orientation relative to a central axis of the shaft. In yet other embodiments, the sensor mount 206 may only include a pedestal that is coupled directly to the shaft and/or connecting element 204.

The pedestal 212 is configured to support, hold, or retain a position sensor in a fixed position with respect to the shaft. The pedestal 212 may include an elongated panel that is sized to engage with the position sensor along an upper surface of the pedestal 212. The pedestal 212 may also include clips, retainers, and/or another suitable fastener to couple the position sensor to the sensor mount 206 and/or to allow for use of the CT guided device 200 with different position sensors or replacement position sensors.

FIG. 3 shows another illustrative CT guided device 300 that includes a shaft having multiple bends including a first bend 307 disposed between a proximal end or base portion 301 and a distal end or tip portion 303 of the shaft, and a second bend 309 disposed between the first bend 307 and the distal end 303. In some embodiments, the second bend 309 is positioned proximate to the distal end 303 (e.g., greater than approximately three quarters of a distance between the first bend 307 and a tip 305 of the distal end 303, etc.). As further shown in FIG. 3, the second bend 309 forms a second angle 311 so that a portion of the shaft between the first bend 307 and the distal end (or tip) is non-linear. The second angle 311 may be within a range between approximately 15 degrees and approximately 75 degrees, inclusive, or another angle between and including the foregoing range (e.g., between approximately 25 degrees and approximately 65 degrees, between approximately 35 degrees and 55 degrees, approximately 45 degrees, etc.). Using multiple bends has been found to simplify insertion into different nasal cavities and/or passages and facilitates manipulation of the distal end when accessing different nasal passages.

The shaft of the catheter 302 may be a hollow tube defining a central passage (e.g., fluid conduit, etc.) that extends between the proximal end 301 and distal end 303 of the shaft. The diameter of the central passage may be approximately constant along a flow direction through the central passage, between the proximal end 301 and the distal end 303 of the shaft, which can facilitate delivery of a numbing agent, or in some cases, an intermediate device (e.g., balloons, cryoprobes, etc.) through the shaft and to the affected region being treated.

As shown in FIG. 3, the tip portion 303 of the shaft extends away from the base portion 301 at an angle of approximately 90 degrees, along an X-axis direction is shown. It should be appreciated that the angle formed between the tip portion 303 and the base portion 301 may be different in other embodiments and may vary depending on the location of the treatment area within the nasal cavity. Together, the first bend 307 and the second bend 309 define three shaft portions, including the base portion 301, the tip portion 303, and an intermediate portion extending between the base portion 301 and the tip portion 303. In the embodiment of FIG. 3, the tip portion and the base portion lie along the same plane (e.g., the XY-plane). However, the tip portion 303 and the base portion 301 may extend along different reference planes in other embodiments.

The base portion 301 may define a first coordinate system 314 centered at a proximal end of the shaft wherein the shaft couples to the connecting element. The first coordinate system 314 may have a Y-axis that extends parallel to a central axis of the base portion 301 of the shaft. The first bend 307 may define a second coordinate system 315 (e.g., a first translated coordinate system, etc.) that is centered at the first bend 307 and having a Y-axis that extends parallel to a central axis of the intermediate portion of the shaft. The second bend 309 may define a third coordinate system 316 (e.g., a second translated coordinate system, etc.) that is centered at the second bend 309 and having a Y-axis that extends parallel to a central axis of the tip portion 303 of the shaft. As will be further described, the first, second, and third coordinate systems may be generated by a CT system, and rotation about different coordinate axis may be monitored using the position sensor to determine a location of the tip portion 303 and a position and/or orientation of a projection from the tip portion 303 or tip 305 (e.g., a projection co-linear with a central axis extending through the tip portion to the tip). Rotational matrices may be used by a CT scanner to define the configuration of the bends 307 and 309, shaft portions, and tip at the distal end of the catheter.

Figure 4:
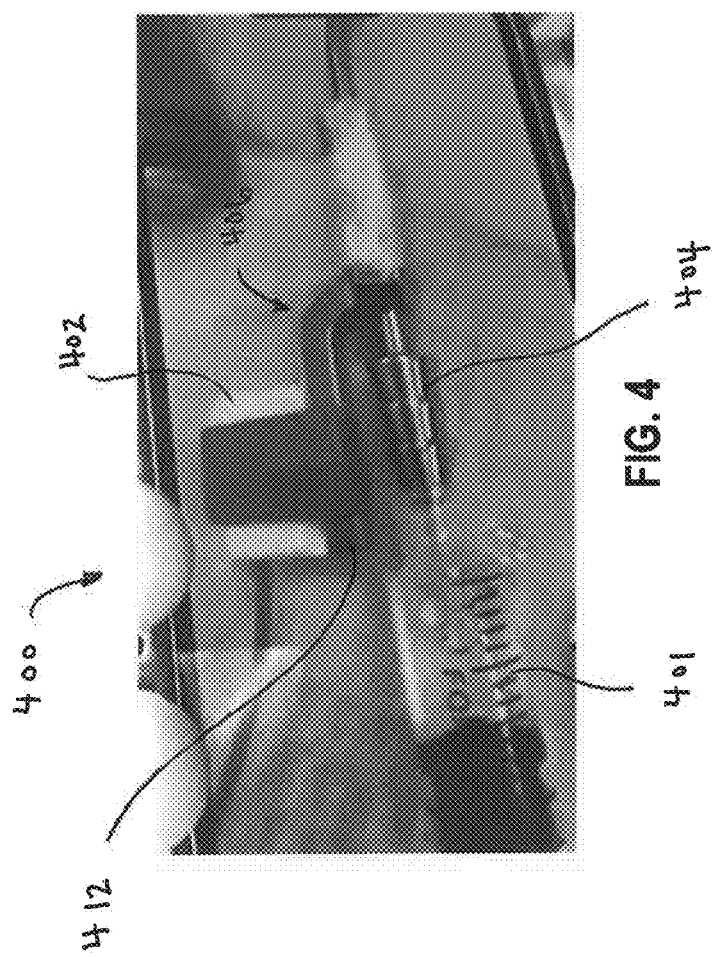
FIG. 4 is an isometric view of another illustrative guided catheter that is connected to a syringe to inject a numbing agent into the catheter.

FIG. 4 shows another illustrative CT guided device 400. The CT guided device 400 is fully assembled to a fluid transfer device 401 and a position sensor 402. The fluid transfer device 401 may be a syringe that is fluidly coupled to a shaft by a connecting element 404. The connecting element 404 may include a barbed tube connection that is coupled to a needle adapter of hub of the syringe. The position sensor 402 is engaged with an upper surface of the sensor mount 406 (e.g., an upper surface of the pedestal) and is coupled to the sensor mount 406 by a clip, which supports the position sensor 402 in fixed position along a pedestal 412 of the sensor mount 406. The position sensor 402 may have a latch or other engaging feature along its length that corresponds with the clip to ensure proper alignment between the position sensor 402 and the pedestal 412 of the sensor mount 406 so as to provide accurate measurements of the position sensor 402 with respect to other parts of the CT guided device 400.

The position sensor 402 is configured to communicate with a CT system (see FIG. 6, for example) to sense a position and/or orientation of a curvilinear shaft (e.g., a non-linear catheter with at least one bend) in real-time, and to generate position data representative of the position and/or orientation. The CT system may be configured to generate a graphical representation of the curvilinear shaft based on the position data, and overlay the graphical representation onto a CT scan that tracks movement of the curvilinear shaft relative to the CT scan and graphically displays a projection from the tip of a catheter to which the fluid transfer device 401 is engaged.

Figure 5:
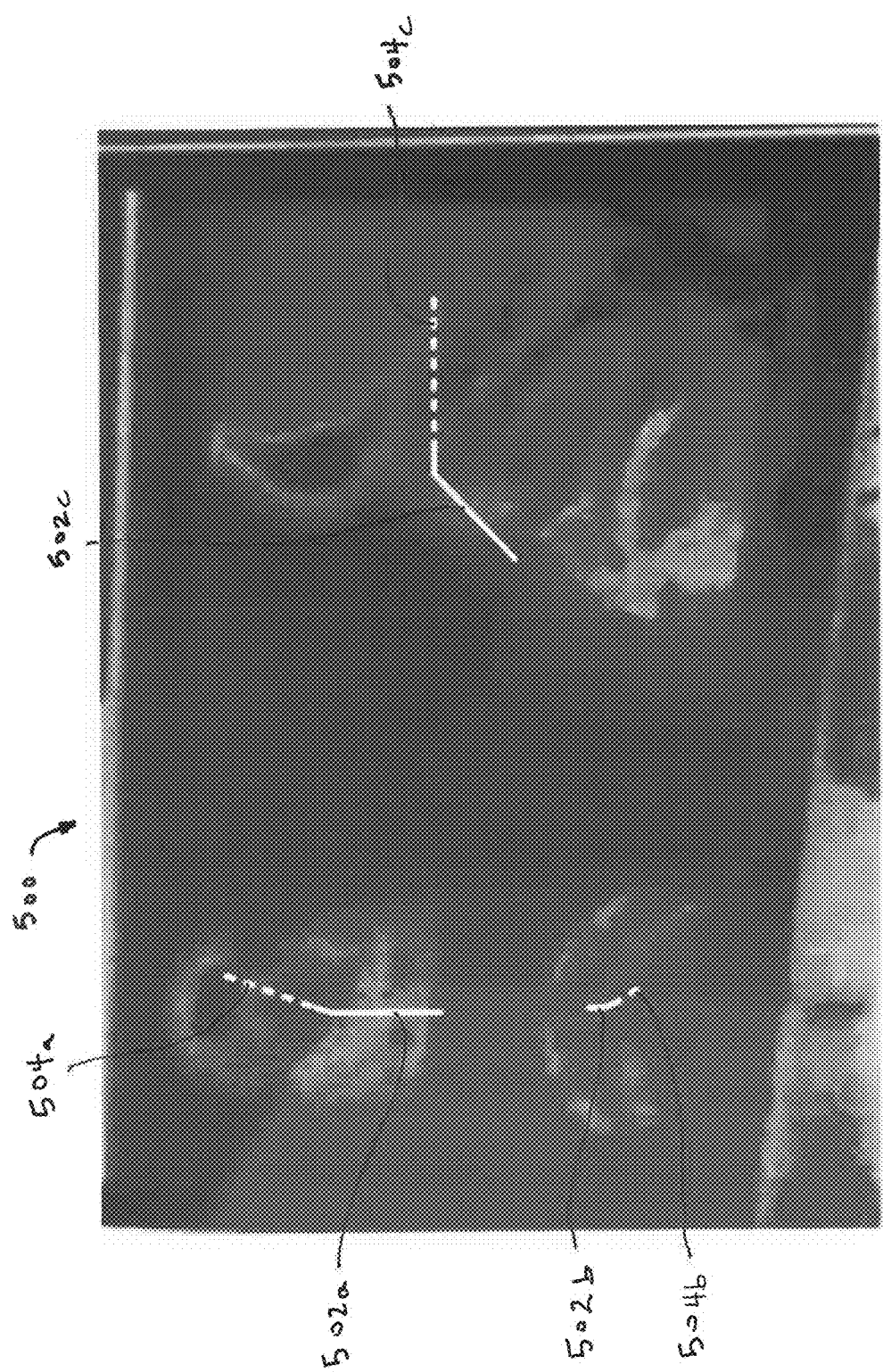
FIG. 5 is a illustrative graphical representation of a guided catheter on a computerized tomography (CT) scan of an anatomical region of a patient.

For example, FIG. 5 shows an illustrative CT scan 500 of an anatomical region of a patient. In particular, the CT scan 500 shows cross-sectional views of a patient's sinus and/or nasal cavity along three different anatomical planes, including the sagittal, coronal, and axial planes. Together, these three views provide a full representation of a curvilinear shaft of a catheter in three dimensions with respect to the patient's sinus and/or nasal cavity. The graphical representation of the position 502a, 502b, 502c of the curvilinear shaft and projection indicator 504a, 504b, 504c extending from a tip of the curvilinear shaft of the catheter may be displayed in all three views in real-time. In this way, a clinician can monitor movement of the curvilinear shaft within the nasal cavity, and ensure that a tip portion or distal end of the shaft is properly positioned and oriented within the nasal cavity during treatment to apply numbing agent or otherwise.

Additionally, the CT system may be configured to generate and dynamically display the projection indicator 504a, 504b, 504c from the tip of the curvilinear shaft in real-time to guide insertion and/or to indicate a region toward which a fluid will be dispensed. The projection indicator 504a, 504b, 504c may be a reference axis that extends from a distal end of the shaft, collinear with a central axis of the distal end, so as to indicate a trajectory of the curvilinear shaft within the nasal cavity. As such, the projection indicator 504a, 504b, 504c may be angularly oriented from a central axis of the base portion of the shaft. It should be appreciated that the CT system may also be configured to overlay multiple projections from the CT guided device, or from different areas of the CT guided device (e.g., a projection from the base portion and/or the intermediate portion) in other embodiments.

Figure 6:
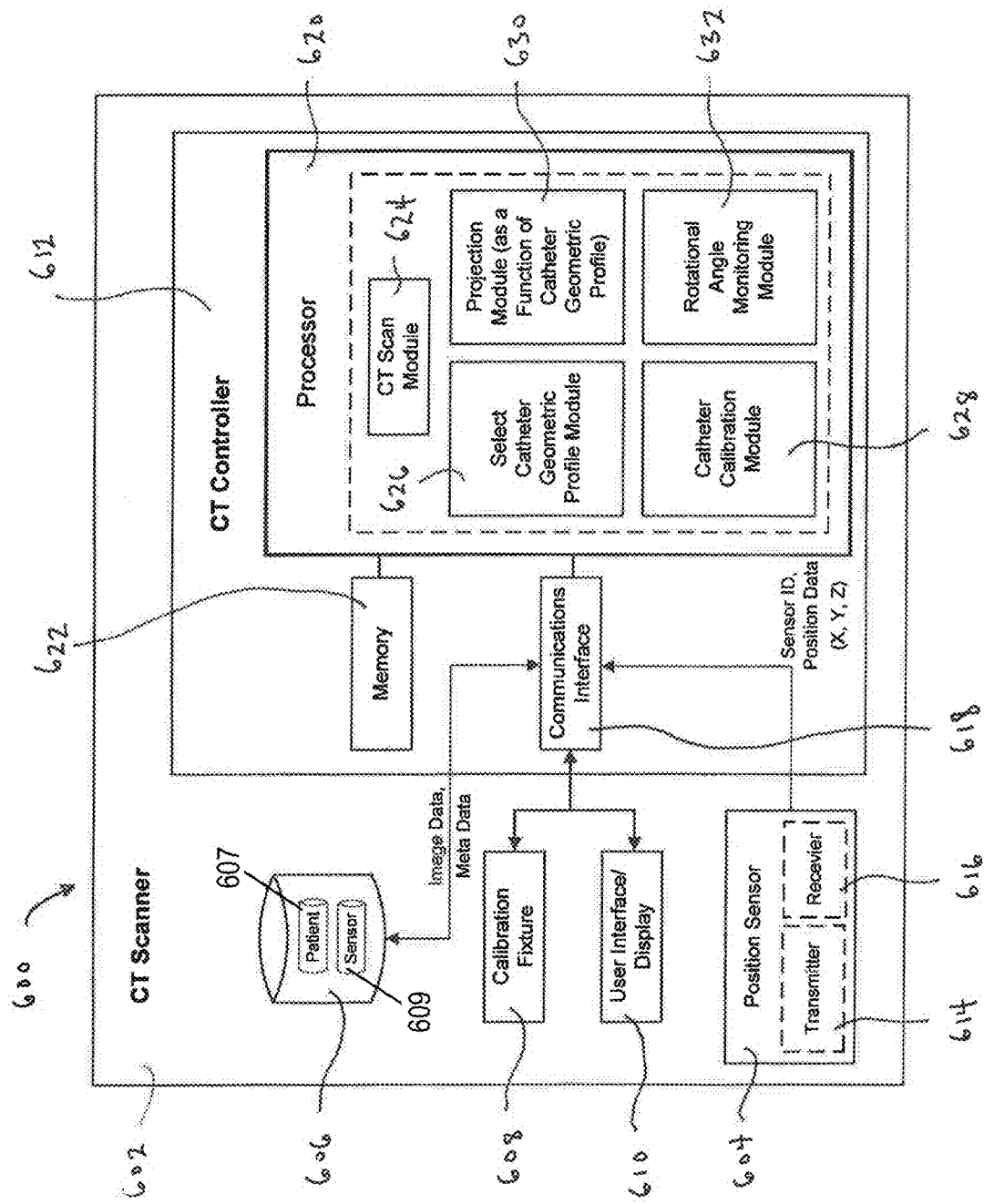
FIG. 6 is a block diagram of an illustrative CT system.

FIG. 6 shows an illustrative CT system 600 that is configured for use with the CT guided device. The CT system 600 includes a CT scanner 602 that is configured to collect CT scan data of an anatomical region of a patient, and to overlay at least portions of the CT guided device onto the CT scan in real-time so as to guide a clinician during treatment. The CT scanner 602 includes a position sensor 604, a patient/sensor database 606, a calibration fixture 608, a user interface 610, and a CT controller 612.

As described above, the position sensor 604 is configured to sense a position and/or orientation of at least a portion of the CT guided device and to generate position data representative of the position and/or orientation. In one embodiment, the position sensor 604 includes an accelerometer or other sensing devices (e.g., gyroscope, inclinometer, or other sensor) that is configured to measure orientation and a direction of force applied to the CT guided device. The position sensor 604 can also determine a position of the CT guided device in three-dimensional space, either by analysis of the accelerometer data or in combination with data measurements from another sensor. The CT guided device may be wired or wireless and utilize any communications protocol with communicating via a wire. In another embodiment, the position sensor 604 may include a transmitter 614 and a receiver 616 that interact to determine a position and/or orientation of the CT guided device. In one embodiment, the transmitter 614 is or includes a fiducial marker that transmits a signal from a fixed position on a patient's body. In such embodiments, the receiver 616 may be configured to receive the signal from the fiducial marker and to transmit the signal data (e.g., strength of signal, etc.) back to the CT system 600. The signal measured by the receiver 616 will vary depending on a relative position of the receiver 616 and the transmitter 614, which allows the CT system 600 to determine a position of the receiver 616 along the X, Y, and Z coordinate axes. In at least one embodiment, the receiver 616 is an electromagnetic receiver that is configured to communicate with an electromagnetic transmitter positioned on the patient, to sense the position and/or orientation of the CT guided device and to communicate the position data to the CT system 600.

The patient/sensor database 606 is configured to store data associated with a patient (shown as patient data 607) and/or sensor data (shown as sensor data 609) associated with the CT guided device. The data associated with the patient may include CT scan data including 3D volumetric data and images taken along different anatomical planes and at different depths. The data associated with the patient may also include meta data, such as a date at which a CT scan was performed, and/or other diagnostic or system information, calibration data, date that the sensor data was collected, etc.

The data associated with the CT guided device may include geometric data corresponding to a profile of different CT guided device designs. The geometry may be inclusive of at least one bend in the shaft of the CT guided device (e.g., the curvilinear shaft). For example, the geometry may identify a length of each linear section of the shaft, the angles formed between each section (at each bend), and a rotational orientation of each section in three dimensions. In at least one embodiment, the geometry of the CT guided device includes coordinates (e.g., in X, Y, and Z axes directions with respect to a base coordinate system for the position sensor) associated with an origin of a coordinate system at each bend. The geometry of the CT guided device may also include data needed for coordinate transformation between each bend of the curvilinear shaft, so as to enable monitoring of a position and/or orientation of different points along the shaft (e.g., the distal end, the tip, an opening at the tip, etc.) in real-time.

The calibration fixture 608 is configured to calibrate a position and/or orientation (e.g., alignment in each of the X, Y, and Z axes) of the position sensor 604 attached to the CT guided catheter and to define a base position and/or orientation during, or in advance of, a treatment regimen. The calibration fixture 608 may be located at a known position and may support the position sensor 604, including the receiver 616 and the transmitter 614 (if included) in fixed orientation. The CT system 600 (e.g., the CT controller 612) may be configured to reset coordinates associated with the relative base position during use of the calibration fixture 608.

The user interface 610 is configured to display a CT scan of an anatomical region of a patient, such as a sinus region based on data received from the CT controller 612. The user interface may include a human-machine interface, which may include an electronic display and a user input device. In at least one embodiment, the human-machine interface includes a touchscreen display that is configured to allow user manipulation of images presented on the display.

The CT controller 612 is configured to control operation of the CT system 600. As shown in FIG. 6, the CT controller 612 includes a communications interface 618, a processor 620, and memory 622. The communications interface 618 is communicably coupled to the position sensor 604, the patient/sensor database 606, the calibration fixture 608, and the user interface 610, and is configured to coordinate communications between each of these components and the CT controller 612. The communications interface 618 may include a network interface card, a transceiver, and/or other electronic communications equipment.

The processor 620 is communicably coupled to the memory 622 and the communications interface 618 and is configured to perform analysis of position data received from the position sensor 604. Memory 622 stores various instructions that, when executed by the processor 620, control at least partly the operation of various components and/or subsystems of the CT system 600. As shown in FIG. 6, the CT controller 612 also includes various modules and/or control circuits. For example, the CT controller 612 includes a CT scan module 624, a select catheter geometric profile module 626, a catheter calibration module 628, a projection module 630, and a rotational angle monitoring module 632. These modules may be embodied as machine or computer-readable media that is executable by the processor and may include instructions (e.g., code) to guide operation of the processor. In another embodiment, the modules may be implemented as hardware units, such as electronic control units, and may include circuitry components for accomplishing any of the operations described herein. In other embodiments, the CT controller 612 may include additional, fewer, and/or different modules to enable the various functionalities of the CT system 600.

The CT scan module 624 may be configured to generate a scan of an anatomical region of a patient. The CT scan module 624 may be configured to transmit commands to, and receive CT scan data from, an X-ray system that is configured to produce a 3D image of soft tissues and bones within the anatomical region of the patient. The CT scan module 624 may be able to display an image of the anatomical region on the user interface (e.g., the electronic display) for review and manipulation by a clinician so that the clinician can examine structures inside the patient's body.

As described above, the CT system 600 is configured to allow tracking, in real-time, of a position and/or orientation of a CT guided device that includes a non-linear geometry, which enables a clinician to utilize catheter/shaft geometries that are tailored for use in treatment of various nasal conditions.

The select catheter geometric profile module 626 may be configured to determine a geometric profile of the CT guided device. The select catheter geometric profile module 626 may be configured to determine the geometric profile based on user inputs. For example, the select catheter geometric profile module 626 may be configured to receive, from the user interface, via the communications interface, an identifier of the CT guided device (e.g., the guided catheter) that is associated with a geometry of the guided catheter. The geometry may include any of the data described above with respect to the patient/sensor database 606. The geometry may be inclusive or representative of the at least one bend in the CT guided device, such as the first bend and/or the second bend in a curvilinear shaft of the CT guided device. For example, the geometry may be described by parameters, such as lengths of portions of the catheter, curve angle(s), or otherwise using any data protocol (e.g., vectors, matrices, etc.). The select catheter geometric profile module 626 may be configured to determine the geometric profile of the CT guided device by accessing a lookup table, stored in memory or retrieved from the patient/sensor database 606, and by iterating through the lookup table to identify the geometric profile that corresponds with the user-prescribed identifier.

In other embodiments, the select catheter geometric profile module 626 may be configured to automatically determine the geometric profile of the CT guided device. For example, the select catheter geometric profile module 626 may be configured to receive data from a position sensor (e.g., the position sensor 604) attached to the CT guided device that includes the indicator. In other embodiments, the select catheter geometric profile module 626 may be configured to automatically determine the indicator based on scan data received from a barcode scanner or another imaging device. The scan data may correspond with a barcode, RF tag, or other identifier that is affixed to the CT guided device.

The rotational angle monitoring module 632 may be configured to determine a real-time position and/or orientation of the CT guided device and curvilinear shaft, and to dynamically display a graphical representation of the position of the CT guided device (and curvilinear shaft) on the CT scan relative to the image of the anatomical region on the electronic display. The rotational angle monitoring module 632 may be configured to receive, via the communications interface 618, position signals, data, and/or measurements from the position sensor. The rotational angle monitoring module 632 may be configured to determine a real-time position and/or orientation of the CT guided device (with the curvilinear shaft) based on the position signals. The position signals may be position data that includes a location of the position sensor 604 in 3D space within or adjacent to the anatomical region, and an orientation of the position sensor 604. The rotational angle monitoring module 632 may be configured to determine the real-time position and/or orientation of different portions of the curvilinear shaft based on (i) the location, and (ii) the geometric profile of the CT guided device (and curvilinear shaft) from the select catheter geometric profile module 626.

In an embodiment, the CT scanner 602 may be calibrated with a position and/or orientation of the CT guided device. For example, the CT guided device may be placed into a fixture that positions and orients the CT guided device in a known position and orientation. The fixture may be connected to or away from the CT scanner itself (e.g., mounted to the front or side of the CT scanner). A calibration mode may be selected when the CT guided device is in the fixture, thereby "zeroing out" the position and/or orientation of the CT guided device as registered by the CT scanner. Thereafter, any motion (position and rotation in X, Y, Z coordinates) of the CT guided device may be sensed and tracked, thereby providing accuracy for the CT scanner when in actual use. It should be understood that alternative techniques for determining position and/or orientation of the CT guided device may be utilized. During use, the CT scanner 602 may use rotational matrices and vectors that describe lengths, bend(s), position, and/or orientation of the CT guided device in displaying a graphical representation on a CT scan of a patient and a projection line as the CT guided device is moved and/or rotated, as further described herein.

For example, and referring to FIG. 2 and FIG. 3, the rotational angle monitoring module 632 may be configured to determine an approximate pitch, yaw, and/or roll of the at least one coordinate system that is associated with a shaft having at least one bend. The pitch, yaw, and/or roll may correspond with an amount of angular rotation about the X, Y, and Z coordinate axes, respectively of the at least one coordinate system (e.g., the first coordinate system as shown in FIG. 2, at least one of the first coordinate system, the second coordinate system, and the third coordinate system as shown in FIG. 3, etc.). The rotational angle monitoring module 632 may determine the position and rotational angle of each portion of the CT guided device based on accelerometer data and or sensor data indicative of spatial position from the receiver of the position sensor 604.

The rotational angle monitoring module 632 may be configured to generate a graphical representation of the shaft of the CT guided device, or a portion of the shaft at the distal end of the shaft (e.g., the tip of the shaft, etc.) based on the spatial position data and the pitch, yaw, and roll. The rotational angle monitoring module 632 may also be configured to overlay the graphical representation of the shaft, or portion thereof, on a CT scan of the patient. For example, the rotational angle monitoring module 632 may be configured to display the graphical representation on anatomical planes (e.g., the sagittal plane, the coronal plane, the axial plane, etc.) presented on the electronic display of the CT system 600, relative to a fiducial marker on the patient. The rotational angle monitoring module 632 may be configured to update the display in real-time based on the position and/or orientation of the CT guided device, enabling a user to navigate across the volumetric image of the anatomical region using the CT guided device as a three-dimensional cursor (see FIG. 5).

The projection module 630 may be configured to display a graphical projection indicator from the distal end and/or tip of the shaft of the CT guided device. For example, the projection module 630 may be configured to generate a reference line/axis extending from a distal end of the shaft, collinear with a central axis of the distal end and/or a central axis of the opening at the tip of the shaft. The reference line may be angled with respect to a central axis at the base portion or proximal end of the shaft. The projection module 630 may be configured to generate the projection indicator (e.g., dashed line, dotted line, colored line different from lines representing the bent catheter) based on geometric profile of the shaft (e.g., as determined by the select catheter geometric profile module), and position signals from the position sensor 604. The projection module 630 may be configured to overlay the projection indicator on the CT scan and to dynamically display the projection indicator alongside the graphical representation of the CT guided device (see FIG. 5). It should be appreciated that the CT system 600 may include additional modules in other embodiments. For example, the CT system 600 may be configured to animate the CT scan during treatment so as to inform the physician of certain operations. In one embodiment, the CT system 600 may be configured to illuminate, color, or otherwise animate the CT scan on the electronic display to indicate regions in which the topical anesthetic is being dispensed.

By enabling real-time monitoring of a position and/or orientation of a CT guided device having a non-linear profile, the CT system of the present disclosure enables treatment of anatomical regions having multiple passages and/or off center-cavities without requiring invasive medical procedures or cutting of patient tissue. In particular, the CT system 600 of the present disclosure can be used to facilitate treatment of various nasal/sinus conditions, which include angled passages, multiple sinus cavities, without requiring sedatives (e.g., general anesthetics), and/or injecting the patient with local anesthetics (e.g., lidocaine) that could increase risk of patient injury (e.g., risk of side effects including temporary blindness, double vision, etc.). By identifying the location of the tip and/or projection from the opening at the tip, a clinician can be more confident that anesthetics are being applied to the right or precise location within the nasal cavity, which can reduce quantities of topical anesthetic required during treatment. In situ CT guidance can also reduce treatment times, improving patient comfort, and further reducing risks during treatment.

A method of operating a CT system, such as the CT system 600 of FIG. 6 may include activating a CT guided device. The method may include receiving signals from a CT guided device and/or detecting the CT guided device upon making a connection to the CT guided device. The method may include setting, by the CT controller 612, a physical configuration of the CT guided device, such as a guided catheter having a bend such that the guided catheter forms an angle. The method may include receiving a device identifier from the CT guided device and retrieving geometry data and rotational matrices associated with the CT guided device from the patient/sensor database 606 based on the device identifier. In one embodiment, the method of receiving the device identifier includes receiving a device identifier input from the user interface that corresponds with the device identifier. The device identifier may include scan data from a barcode or another form of machine-readable text. In another embodiment, receiving the device identifier includes receiving identifier data from the device through the connection to the device (e.g., via circuitry onboard the CT guided device, etc.).

The method may include calibrating the position sensor 604 (e.g., by the catheter calibration module 628) that is attached to the CT guided device to define a relative base position and/or orientation of the position sensor 604, at least one bent portion of the shaft of the CT guided device, the tip of the CT guided device, and/or a tip projection extending axially away from the CT guided device. The method may include calibrating the CT guided device by "zeroing out" or otherwise applying position data (e.g., calibration data, etc.) from the memory 622 and/or received from the calibration fixture 608 to data from the position sensor 604 onboard the CT guided device. The method may include determining (e.g., by the select catheter geometric profile module 626) relative positions and/or rotational matrices for the CT guided device, the catheter, etc. based on the sensor data stored in the patient/sensor database 606. The method of calibration the CT guided device may include receiving an indication from the user interface 610 and/or the calibration fixture 608 that the CT guided device has been placed in the calibration fixture 608 and automatically applying calibration data to the signals received from the CT guided device.

In some embodiments, the method includes displaying an image of an anatomical region of a patient via the user interface 610 (such as on an electronic display). The method may include performing a scan of the anatomical region of the patient (e.g., by the CT scan module 624) and generating the image based on the scan. The method may include retrieving the image from the patient/sensor database 606 (e.g., from a patient profile) based on inputs received from the user interface 610.

The method may include receiving position signals from the position sensor 604 that is connected to the CT guided device and displaying (e.g., by the projection module 630) a graphical representation of the CT guided device (e.g., a guided catheter, etc.) relative to the image of the anatomical region of the patient being displayed in real-time. The method of displaying the graphical representation may include overlaying an image of the CT guided device, including the shaft, bends in the shaft, the tip of the shaft of the CT guided device.

In some embodiments, the method includes determining a location and/or orientation of a tip projection extending axially away from the tip of the shaft of the CT guided device. The method may include determining the location and/or orientation of the tip projection as a function of the physical configuration of the CT guided device based on sensor data from the patient/sensor database 606. The location and/or orientation of the tip projection may be angularly oriented from an axial axis of a base portion of the shaft of the CT guided device prior to a bend in the shaft of the CT guided device. The method may include generating a graphical projection indicator from the tip of the CT guided device based on the location of the tip projection and overlaying the graphical projection indicator onto the image of the anatomical region. The method may include displaying the graphical projection indicator overlaid onto the image of the anatomical region and the graphical representation of the CT guided device via the user interface 610 (e.g., through the electronic display).

The method may include dynamically updating (e.g., by the rotational angle monitoring module 632) images on the electronic display in real-time based on data from the position sensor 604 to indicate a real-time location of the CT guided device and tip projection (e.g., the graphical projection indicator) relative to the patient's body. It should be appreciated that any of the foregoing operations may be performed by single control system or by multiple separate control systems working together (e.g., a CT control system and a calibration system that communicates with the CT control system, etc.). In other embodiments, the method may include additional, fewer, and/or different operations.

Figure 7:
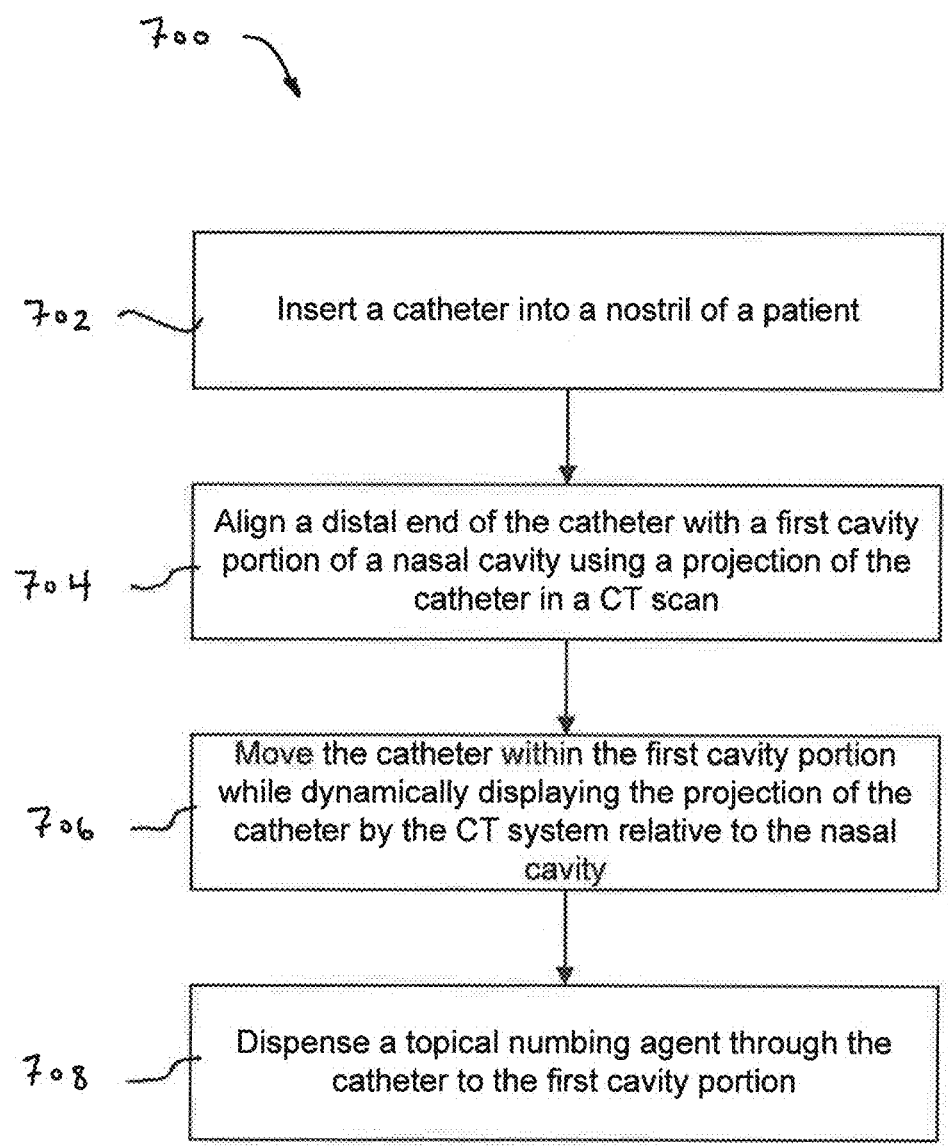
FIG. 7 is a flow diagram of an illustrative method of applying a topical numbing agent to a nasal cavity using a guided catheter.

FIG. 7 is a flow diagram that shows an illustrative method 700 of applying a topical numbing agent to a nasal cavity. The method 700 may be performed without sedating a patient, and may provide sufficient numbness to enable further treatment (e.g., such as cryoablation, balloon sinuplasty, etc.) while the patient remains awake. The method 700 may be performed using the CT system of FIG. 6 using the CT guided device of any one of FIGS. 2-4.

At 702, a portion of a CT guided device is inserted into a nostril of a patient. The CT guided device may include a curvilinear shaft having at least one bend and forming a first angle (e.g., resulting from a bend) such that at least a portion of the catheter is non-linear. Step 702 may include inserting a distal end of a non-linear shaft of the CT guided device into the nostril. Step 702 may also include performing a pre-operative CT scan of the patient using an X-ray device (obtaining a baseline CT scan of the patient's head and/or sinus/nasal cavities. The pre-operative scan may include affixing a fiducial marker and/or electromagnetic transmitter to the patient to provide a reference point along the CT scan during imaging. Additionally, step 702 may include calibrating the CT guided device using the calibration fixture and to set a base reference of the position sensor with respect to the fiducial marker.

The method 700 may also include guiding a distal end of the curvilinear shaft into a nasal cavity using a CT system. For example, the method 700 may include aligning the distal end of the shaft with a first cavity portion of the patient's nasal cavity (at step 704). The first cavity portion may be a middle meatus, sphenoid sinus, frontal sinus, or any other target cavity or passage within the patient's nose and sinuses. Step 704 may include using a graphical representation of the shaft along at least two axis directions to assist the surgeon in determining a current position of the shaft. Step 704 may also include aligning the distal end using a projection of the catheter within the nasal cavity on a CT scan of the patient. Step 704 may further include aligning the projection with the first cavity portion along at least two anatomical planes of the patient. In some embodiments, step 704 may further include referring to a camera view from a tip portion of the shaft (e.g., via an endoscope) to confirm the position and/or orientation of the shaft within the nasal cavity.

Guiding the distal end into the nasal cavity also includes moving the shaft within the first cavity portion while dynamically displaying the graphical representation and projection of the catheter by the CT system relative to the nasal cavity (at step 706). For example, step 706 may include moving the CT guided device (e.g., top portion of the shaft) along the projection extending toward the first cavity portion. Step 706 may include referencing the graphical representation and projection along at least two anatomical planes to confirm that the tip portion does not deviate from the desired target position during movement.

At step 708, the clinician dispenses the topical numbing agent through the catheter to the first cavity portion. Step 708 may include depressing or otherwise activating a syringe or other fluid transfer device that is attached to the CT guided device to dispense topical numbing agent onto a surface of the tissue at the first cavity (e.g., a sphenoid sinus, a frontal sinus, etc.). For example, step 708 may include dispensing approximately 3 mL of Tetracaine or another topical anesthetic to the tissue surface without injecting the CT guided device into the tissue. Beneficially, by using the guided CT method described herein, a clinician may require lower quantities of topical anesthetic to perform treatment because the topical numbing agent can be applied more accurately and with less uncertainty than is achievable using unguided treatment methods. For example, a clinician may require no more than 1.5 mL, or less, to sufficiently numb the treatment area.

In at least one embodiment, the method 700 further includes applying topical anesthetic to another portion of the nasal cavity, such as a second cavity portion, depending on the procedure being performed. Such additional treatment can be performed by repeating steps 702-708. The method 700 may also include using the CT system to guide treatment of cryotherapy instruments and/or balloons, depending on the patient's nasal condition.

As utilized herein, the term "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

While the instant disclosure has been described above according to its preferred embodiments, it can be modified within the spirit and scope of this disclosure. This application is therefore intended to cover any variations, uses, or adaptations of the instant disclosure using the general principles disclosed herein. Further, the instant application is intended to cover such departures from the present disclosure as come within the known or customary practice in the art to which this disclosure pertains.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It is noted that any element disclosed in one embodiment may be incorporated or utilized with any other embodiment disclosed herein.

What is claimed is:

1. A computerized tomography (CT) guided device, comprising:
   a catheter having a proximal end, a distal end, and a shaft extending therebetween, the shaft including a first bend that forms a first angle such that at least a portion of the catheter is non-linear;
   a position sensor coupled to the catheter at the proximal end, and configured to output first position data thereof; and
   a computerized tomography controller configured to:
      sense a position and/or orientation of the catheter utilizing the first position data from the position sensor;
      generate second position data representative of the position and/or orientation of the catheter; and
      display a graphical projection indicator extending away from the catheter that indicates a trajectory of at least one portion of the catheter based on the second position data.

2. The computerized tomography guided device of claim 1, wherein the catheter is configured to dispense a topical numbing agent to a tissue surface.

3. The computerized tomography guided device of claim 1, wherein the first angle is between approximately 45 degrees and about 75 degrees.

4. The computerized tomography guided device of claim 1, wherein the catheter further includes a second bend between the first bend and the distal end, the second bend forming a second angle.

5. The computerized tomography guided device of claim 4, wherein the second angle is between approximately 15 degrees and approximately 75 degrees.

6. The computerized tomography guided device of claim 1, wherein the position sensor includes an electromagnetic receiver, the electromagnetic receiver configured to communicate with an electromagnetic transmitter to sense the position and/or orientation of the catheter and communicate the first position data to the computerized tomography controller.

7. The computerized tomography guided device of claim 1, wherein the computerized tomography controller is further configured to dynamically display a graphical representation of the catheter relative to an anatomical region of a patient on a computerized tomography scan based on the first position data.

8. The computerized tomography guided device of claim 7, wherein the shaft defines a fluid pathway that extends from the distal end of the catheter, wherein the computerized tomography controller is further configured to display the graphical projection indicator extending axially from the fluid pathway at the distal end on the computerized tomography scan to indicate a trajectory from the fluid pathway.

9. The computerized tomography guided device of claim 1, wherein the computerized tomography controller is further configured to:
   determine an angle relative to a central axis of the shaft at the proximal end of the catheter; and
   display the graphical projection indicator extending axially away from the distal end of the catheter and oriented at the determined angle relative to the central axis of the shaft at the proximal end.

10. The computerized tomography guided device of claim 1, wherein the computerized tomography controller is further configured to:
    determine lengths of the graphical projection indicator in at least two anatomical planes through an anatomical region of a patient, the lengths of the graphical projection indicator being different in each of the at least two anatomical planes; and
    display the graphical projection indicator utilizing the determined lengths in the at least two anatomical planes.

11. The computerized tomography guided device of claim 10, wherein determining the lengths of the graphical projection indicator includes computing the lengths in each of a sagittal plane, a coronal plane, and an axial plane taken through the anatomical region of the patient.

12. The computerized tomography guided device of claim 1, wherein the computerized tomography controller utilizes at least one rotational matrix to define the position and/or orientation of the first bend.

13. The computerized tomography guided device of claim 1, wherein the computerized tomography controller, in generating the second position data, is further configured to generate the second position data relative to initial calibration data stored in a non-transitory memory.

* * * * *